(12) United States Patent
Koo

(10) Patent No.: US 6,829,940 B2
(45) Date of Patent: Dec. 14, 2004

(54) METHOD AND APPARATUS FOR MEASURING SURFACE WAVE TRAVELING TIME

(75) Inventor: Lat Sang Koo, Hamilton, OH (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 10/161,198

(22) Filed: May 31, 2002

(65) Prior Publication Data

US 2003/0221489 A1 Dec. 4, 2003

(51) Int. Cl.[7] .............................................. G01N 29/04
(52) U.S. Cl. ............................ 73/597; 73/602; 73/628; 73/644
(58) Field of Search .......................... 73/597, 600, 602, 73/603, 606, 627, 628, 643, 644, 1.82, 1.84

(56) References Cited

U.S. PATENT DOCUMENTS

| | | | | |
|---|---|---|---|---|
| 4,338,820 A | * | 7/1982 | Jassby et al. ................. | 73/597 |
| 4,375,165 A | | 3/1983 | de Sterke .................... | 73/622 |
| 4,492,117 A | * | 1/1985 | Chubachi .................... | 73/597 |
| 4,524,621 A | * | 6/1985 | Yamanaka ................... | 73/597 |
| 4,964,295 A | | 10/1990 | Nottingham et al. ...... | 73/1 DV |
| 4,991,427 A | | 2/1991 | Nottingham et al. ......... | 73/623 |
| 5,079,952 A | * | 1/1992 | Nakaso et al. ............... | 73/624 |
| 5,211,059 A | * | 5/1993 | Hayakawa et al. .......... | 73/606 |
| 5,269,188 A | * | 12/1993 | Esin et al. ................... | 73/610 |
| 5,307,680 A | * | 5/1994 | Drescher-Krasicka ....... | 73/606 |
| 5,349,862 A | * | 9/1994 | Chubachi et al. ............ | 73/602 |
| 5,549,001 A | | 8/1996 | Brokowski et al. .......... | 73/597 |
| 6,070,468 A | * | 6/2000 | Degertekin et al. .......... | 73/644 |
| 6,279,396 B1 | * | 8/2001 | Imagawa et al. ............ | 73/597 |
| 6,286,370 B1 | * | 9/2001 | Sinha .......................... | 73/579 |
| 6,575,036 B1 | * | 6/2003 | Huang et al. ................ | 73/597 |

OTHER PUBLICATIONS

L.S. Koo and K.L. Telschow, "Analysis of Laser Ultrasonic Measurments of Surface Waves on Elastic Spheres", published in Review of Progress in Qualtitive Nondestructive Evaluation, vol. 11 (1992).

R.S. Gilmore, "Industrial Ultrasonic Imaging and Microscopy", published in J. Phys. D: Appl Phys. 29 (1996).

* cited by examiner

Primary Examiner—Hezron Williams
Assistant Examiner—Jacques M. Saint-Surin
(74) Attorney, Agent, or Firm—William Scott Andes; Armstrong Teasdale LLP

(57) ABSTRACT

A method is provided for measuring the surface travel time of a surface wave between first and second points on a surface. First and second spaced apart transducers are disposed substantially perpendicular to a surface. The direct travel times for each transducer are determined, then a total travel time from the first transducer to the second transducer is measured. The direct travel times are subtracted from the total travel time to produce the actual travel time between the points on the surface.

9 Claims, 6 Drawing Sheets

US 6,829,940 B2

METHOD AND APPARATUS FOR MEASURING SURFACE WAVE TRAVELING TIME

BACKGROUND OF THE INVENTION

This invention relates generally to ultrasonic testing and more particularly to measurement methods in ultrasonic testing.

Ultrasonic surface waves are often employed to detect or characterize near surface residual stresses, material property changes, surface roughness, defects, etc. in a specimen. Typically an immersion ultrasonic technique is used, wherein one or more transducers are acoustically coupled to a specimen by a coupling medium, for example liquid water. Ultrasonic waves can then be transmitted from the transducer to the specimen and back through the coupling medium. One of the most important quantities measured in such a technique is the traveling time of a surface wave between two points on the surface of the test specimen. Using the prior art immersion ultrasonic technique, there is no practical method to accurately extract this true surface wave traveling time from the total traveling time of the ultrasonic wave going from the transmitting transducer to the receiving transducer. This total traveling time includes not only the true surface wave traveling time in the specimen, but also the traveling time of the wave through the coupling medium between the specimen and the transducers.

Accordingly, there is a need for a practical method of accurately measuring the true surface wave traveling time between two points on a specimen.

BRIEF SUMMARY OF THE INVENTION

The above-mentioned need is met by the present invention, which provides a method and apparatus for measuring the surface travel time of a surface wave between first and second points on a surface. First and second spaced apart ultrasonic transducers are disposed with their longitudinal axes substantially perpendicular to a surface. The direct travel times for each transducer are determined, then a total travel time from the first transducer to the second transducer is measured. The direct travel times are subtracted from the total travel time to compute the actual travel time between the points on the surface.

The present invention and its advantages over the prior art will become apparent upon reading the following detailed description and the appended claims with reference to the accompanying drawings.

BRIEF DESCRIPTION OF THE DRAWINGS

The subject matter that is regarded as the invention is particularly pointed out and distinctly claimed in the concluding part of the specification. The invention, however, may be best understood by reference to the following description taken in conjunction with the accompanying drawing figures in which:

DETAILED DESCRIPTION OF THE INVENTION

Figure 1:
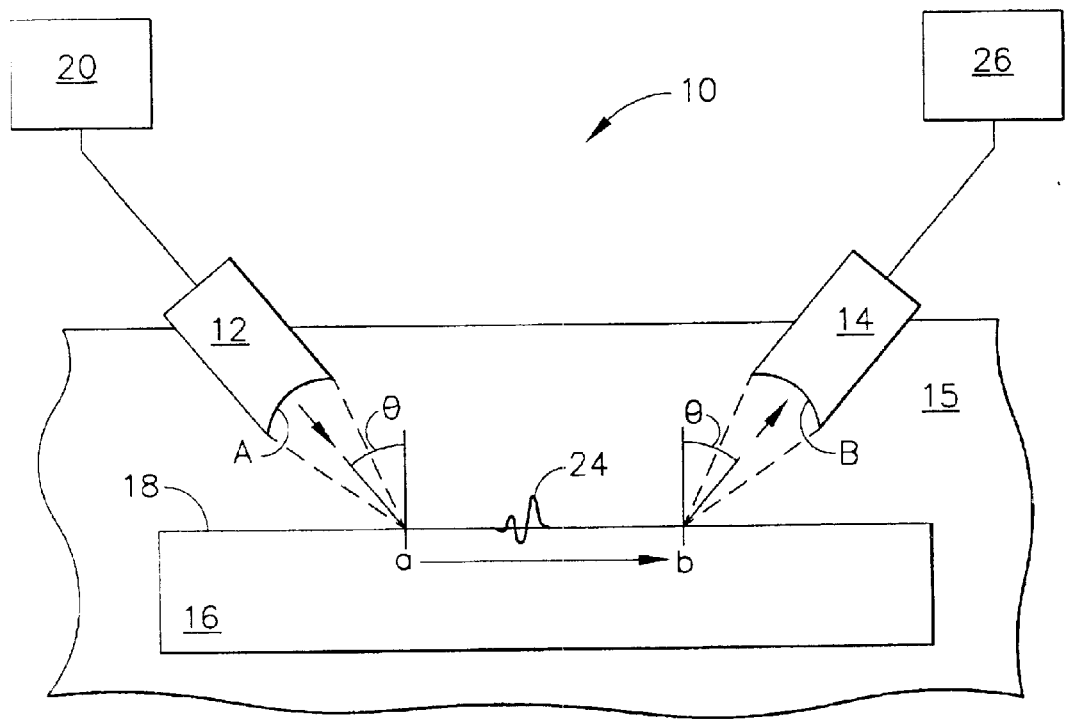
FIG. 1 is a schematic illustration of a prior art pitch-catch ultrasonic transducer arrangement.

Referring to the drawings wherein identical reference numerals denote the same elements throughout the various views, FIG. 1 illustrates a prior art method used to measure surface wave traveling time in a specimen with an immersion ultrasonic technique. A so-called pitch-catch setup 10 is used. The setup 10 includes a first transducer 12 and a second transducer 14, which are both immersed in a coupling medium 15, which is typically water, along with the specimen 16, which has a surface 18. As an alternative approach, some immersion ultrasonic systems fill the sound paths of both transducers with a coupling medium by continuously shooting a stream of coupling fluid from a squirter attached to the transducer. With either setup, both transducers 12 and 14 are tilted at a critical angle θ where $$\theta = \sin^{-1}\left(\frac{v_m}{v}\right) \qquad (1)$$

and $v_m$ is the acoustical speed of the coupling medium while v is the acoustical speed (usually the longitudinal mode) of the specimen 16.

In operation, the transmitting transducer (e.g., first transducer 12) is pulsed by a pulser 20 connected to the first transducer 12. This creates an ultrasonic wave in the coupling medium 15 which travels from the surface of the first transducer 12, labeled A in FIG. 1, to a first point on the surface 18 of the specimen 16, labeled point a. At point a, because the incident wave hits the specimen 16 at the critical angle θ, most of the induced mechanical waves in the specimen 16 stay near the surface 18 as surface ultrasonic waves (one wave front is schematically illustrated as item 24 in FIG. 1). The created surface waves will continue to travel toward a second point on the surface 18 of the specimen 16, labeled point b, and beyond. Along its wave path, the surface wave 24 continuously releases energy back into the coupling medium 15. When the surface wave 24 arrives at point b, the released energy travels towards the second transducer 14, and is received at its surface B. The received wave is then recorded by a receiver 26 connected to the second transducer. From FIG. 1, it can be seen that the total transmitted time from transducer surface A to transducer surface B is a summation of a surface traveling time from transducer surface A to point a (time $t_{Aa}$), plus traveling time from point a to point b (time $t_{ab}$), plus traveling time from point b to transducer B (time $t_{bB}$), that is, $t_{AB} = t_{Aa} + t_{ab} + t_{bB}$. Because the longitudinal axes of transducers 12 and 14 are tilted at a substantial angle away from perpendicular to the surface 18 (typically in the range of 13° to 25° for most structural metals), an individual transducer will not receive significant direct reflection of the wave transmitted by that transducer. Thus, the prior art offers no direct way to extract the surface traveling time between points a and b ($t_{ab}$), which is the quantity of interest, from the total transmitted time ($t_{AB}$). Although the travel times $t_{Aa}$ and $t_{bB}$ may be estimated, this may be accomplished only with expensive and complicated procedures and equipment in a scientific laboratory but not in an industrially pragmatic manner. The difficulty of estimating the times $t_{Aa}$ and $t_{bB}$ is further increased because the acoustic velocities $v_m$ and $v$ depend not only on the material properties of the coupling fluid 15 and the specimen 16, but also on their temperatures. Especially in the coupling fluid 15, the velocity $v_m$ is sensitive to even small changes in temperature. This factor adds additional corruption to the result when attempting to approximate the surface wave traveling time using the total traveling time from one transducer to the other.

Figure 2:
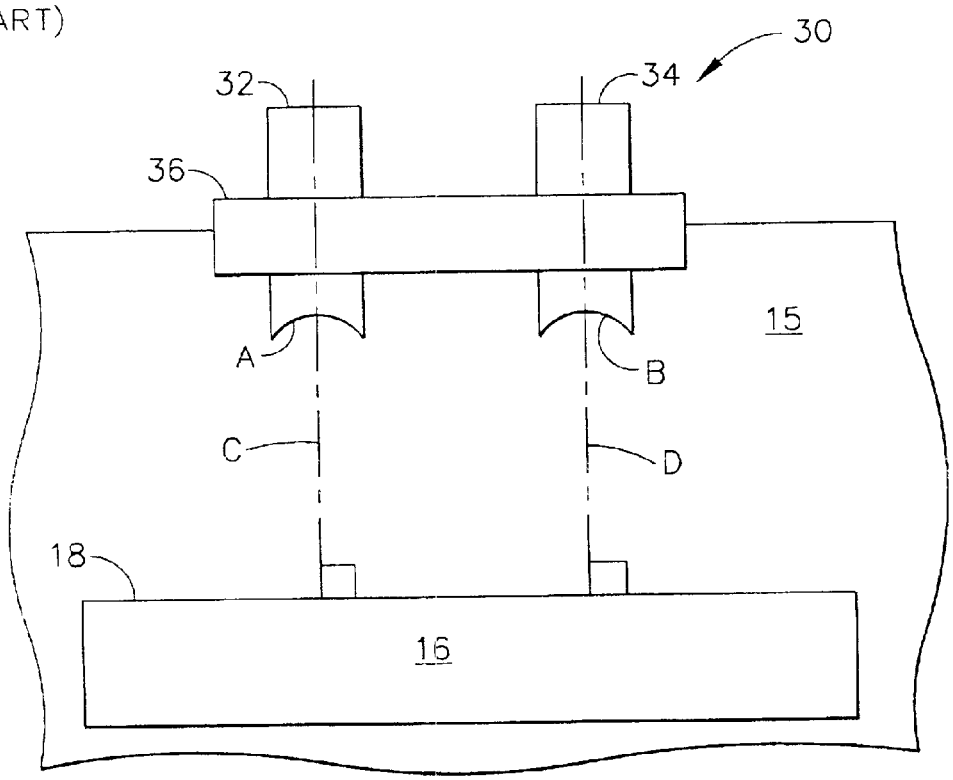
FIG. 2 is a schematic illustration of an ultrasonic transducer arrangement for practicing the method of the present invention.

The present invention provides a method which allows the accurate determination of the surface traveling time by a simple subtraction procedure. An exemplary apparatus 30 for practicing the present invention is shown in FIG. 2. The apparatus 30 includes a first ultrasonic transducer 32 and a second ultrasonic transducer 34. In the illustrated example the transducers are focusing-type transducers whose surfaces, labeled A and B, are concave. One example of a usable transducer is a broad band, 2.25 MHz transducer, having a 12.7 mm (0.5 in.) diameter and a 2.54 cm (1 in.) spherical focal length. With two focusing transducers, the optimal signal-to-noise ratio can be obtained by focusing at the surface 18 of the specimen 16 in a known manner. Other transducer arrangements, such as a combination of focusing and flat transducers, or two flat transducers, could also be used. The transducers 32 and 34 are mounted to a transducer holder 36 which fixes the transducers in a parallel, spaced-apart relationship to each other. The holder 36 is then mounted by known means so that the longitudinal axes of the transducers 32 and 34 (labeled C and D in FIG. 2) are perpendicular to the surface 18 of the specimen 16. This relative positioning of the transducers ensures that a direct reflection of the wave sent by a transducer will be received at that transducer.

The transducers 32 and 34 need not be mounted with their longitudinal axes exactly perpendicular to the surface 18. They may be tilted away from perpendicular by a few degrees in either direction, with the result of decreased accuracy in the measurement of the direct reflection travel time. However, to obtain the maximum benefit of the present invention their longitudinal axes should be mounted substantially perpendicular to the surface 18.

Figure 4:
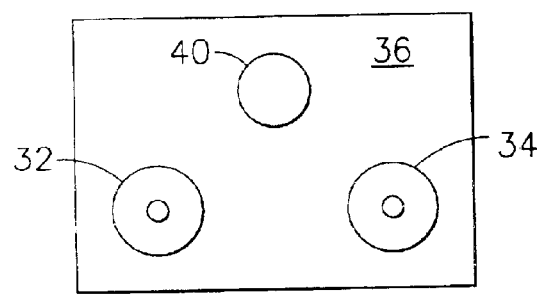
FIG. 4 is a top view of the transducer holder of FIG. 3.
Figure 3:
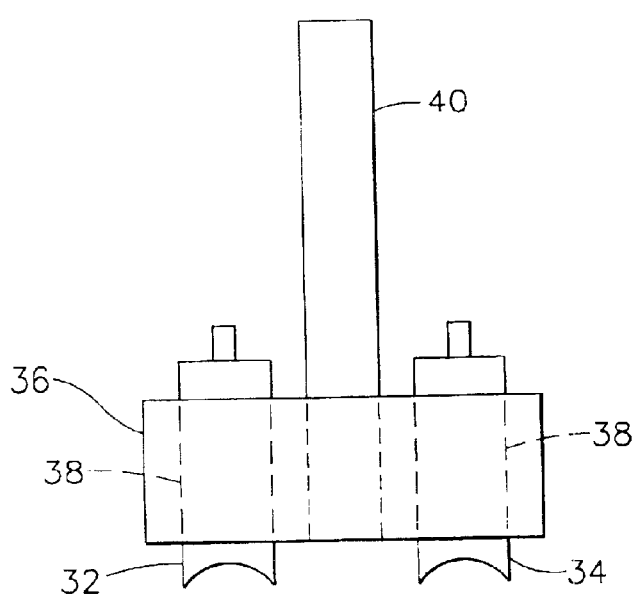
FIG. 3 is a front view of an exemplary transducer holder for use with the present invention.
Figure 5:
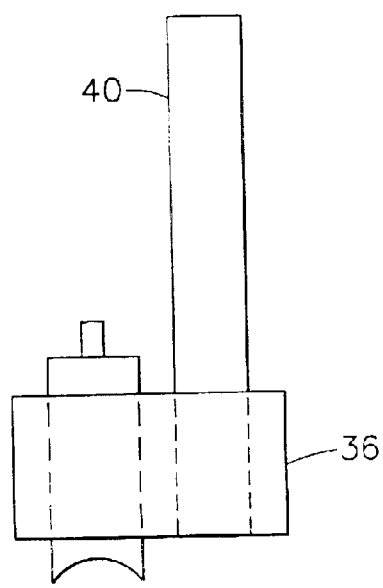
FIG. 5 is a side view of the transducer holder of FIG. 3.
Figure 11:
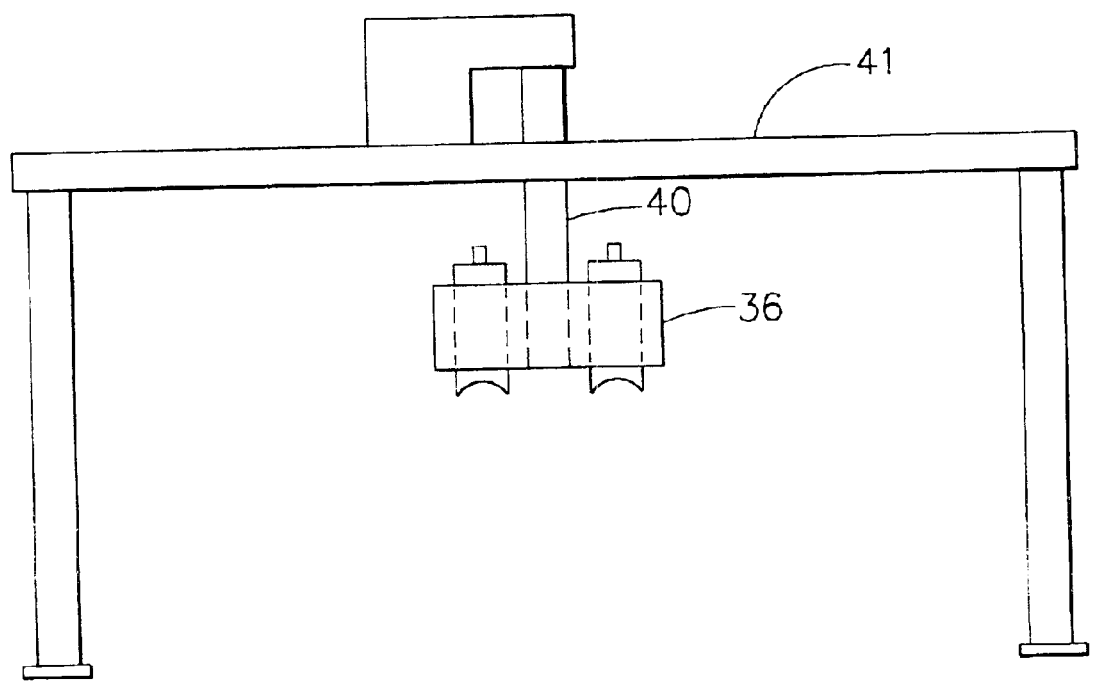
FIG. 11 is a schematic view of the exemplary transducer holder of FIG. 3 mounted on an ultrasonic scanning bridge.

An exemplary embodiment of a holder 36 is illustrated in FIGS. 3, 4, and 5. The holder 36 comprises a simple rectangular bar. A pair of holes 38 are formed in the holder 36. The diameter of the holes 38 is slightly larger than the outer diameter of the transducers 32 and 34 so as to create a snug fit. The transducers 32 and 34 are placed in the holes 38. This fixes the transducers 32 and 34 in the desired relationship. The holder 36 includes suitable mounting means, such as an attachment rod 40, so that it may then be mounted to an appropriate structure 41, such as a known ultrasonic scanning bridge (shown schematically in FIG. 11) to position the transducers so that their longitudinal axes C and D are perpendicular to the surface 18 of the specimen 16, as shown in FIG. 2. Such ultrasonic scanning bridges are available from Sonix, Inc., 8700 Morrissette Drive, Springfield, Va. 22152. The holder 36 may be constructed of any material that is stable and that does not absorb water (or other chosen coupling medium). In the illustrated example the holder 36 is made from PLEXIGLAS G acrylic sheet. Other designs may be used for the holder 36, however, the exemplary embodiment presented is simple and inexpensive to construct.

Figure 6:
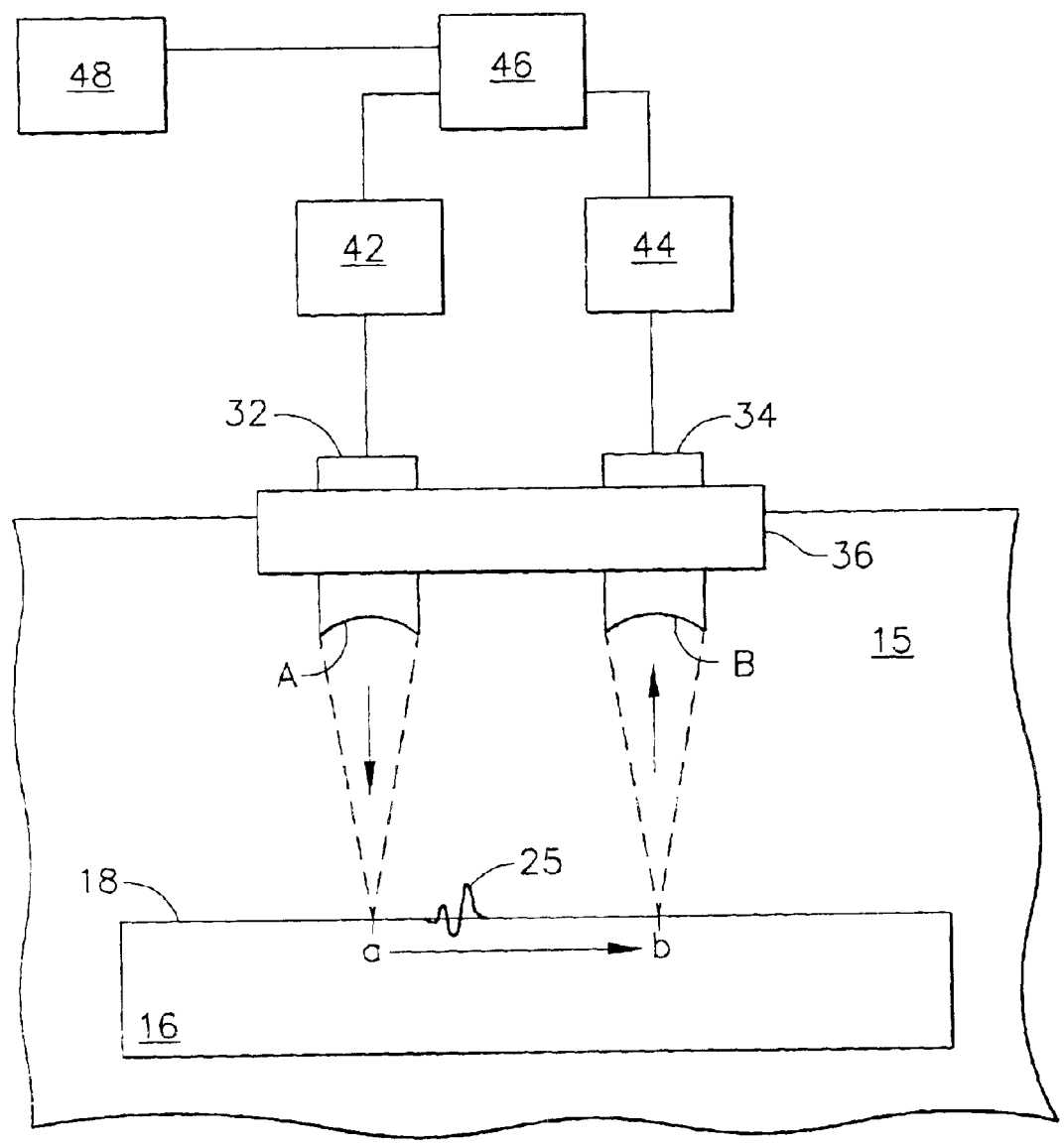
FIG. 6 is a schematic view of the ultrasonic transducer setup for practicing the method of the present invention by a first procedure.

The first and second transducers 32 and 34 are connected to appropriate ultrasonic test equipment, as shown in FIG. 6. For example, the first transducer may be connected to an ultrasonic pulser 42 while the second transducer is connected to an ultrasonic receiver 44. The ultrasonic pulser and receiver are of known types. It is also noted that the functions of pulser and receiver may be combined in a single unit. As used herein, the term "pulser" is intended to refer to a individual unit as well as a component or group of components within a larger device capable of transmitting signals to a transducer, while the term "receiver" is intended to refer to a individual unit as well as a component or group of components within a larger device capable of receiving signals from a transducer. One example of a suitable combined unit is a PR50-S Pulser/Receiver available from JSR Ultrasonics, 3800 Monroe Ave., Pittsford, N.Y. 14534. This exemplary unit incorporates a pulser having a maximum pulse amplitude of 210 V at 250 Ω, and a receiver with a maximum gain setting of 50 dB. Both the pulser 42 and receiver 44 (whether separate or part of a combined unit) are connected to a data acquisition unit 46 of a known type (for example a FlexSCAN-C unit made by Sonix, Inc., 8700 Morrissette Drive, Springfield, Va. 22152) which is in turn connected to a computer 48, such as an IBM PC-compatible computer. Appropriate known software is then used to record the waveforms generated by the pulser and received by the receiver and to compute the various travel times. It is noted that the method of the present invention is independent of the additional equipment described above (i.e. the data acquisition unit 46 and computer 48) and could also be accomplished with other types of measurement equipment, for example a known digital or analog oscilloscope could be connected to the pulser and the receiver and used to measure the wave travel times.

The arrangement of the transducers 32 and 34 perpendicular to the surface 18 of the specimen 16 does not theoretically favor the generation of surface waves, because the longitudinal axes of the transducers are not disposed at the critical angle with respect to the surface 18. However, it has been found in practice that the transducers do not generate solely a narrow pencil beam, because of the spherical shape in the case of a focusing transducer, or because of the natural divergence of waves created by a flat transducer. Therefore, either type of transducer generates acoustic energy in multiple directions, at least a portion of which creates surface waves in the specimen 16. Furthermore, it is surmised that surface waves may also be generated in the specimen 16 by the mechanism of dynamic loading, similar to that which has been observed in known laser ultrasonic systems. Regardless of their exact causation, it has been found that surface waves can be detected at the receiver 44 by using a pulser 42 of sufficient output and by increasing the gain setting of the receiver 44 connected to the receiving transducer. For example, using a PR50-S pulser with a 210 V pulse amplitude, the accompanying receiver at a gain setting of 50 dB, and the transducer arrangement described above, results in the generation of measurable surface waves. Although using a high gain setting in this manner also amplifies noise in the output data, the arrival of a surface wave at the receiving transducer is still sufficiently discernable for purposes of measuring the wave travel time.

Figure 7:
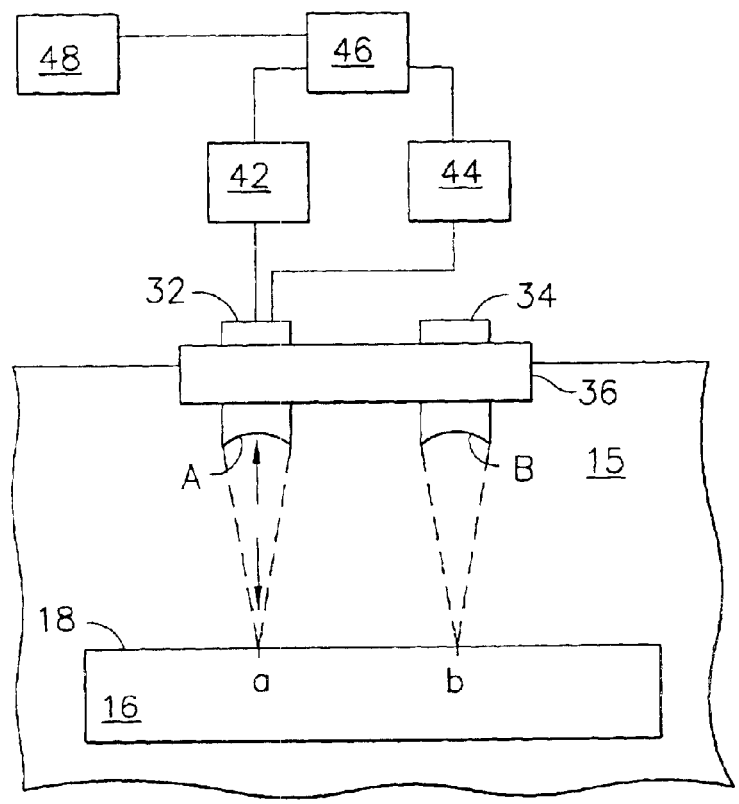
FIG. 7 is a schematic view of the ultrasonic transducer setup of FIG. 6 illustrating a first intermediate arrangement of connections between the various components.
Figure 8:
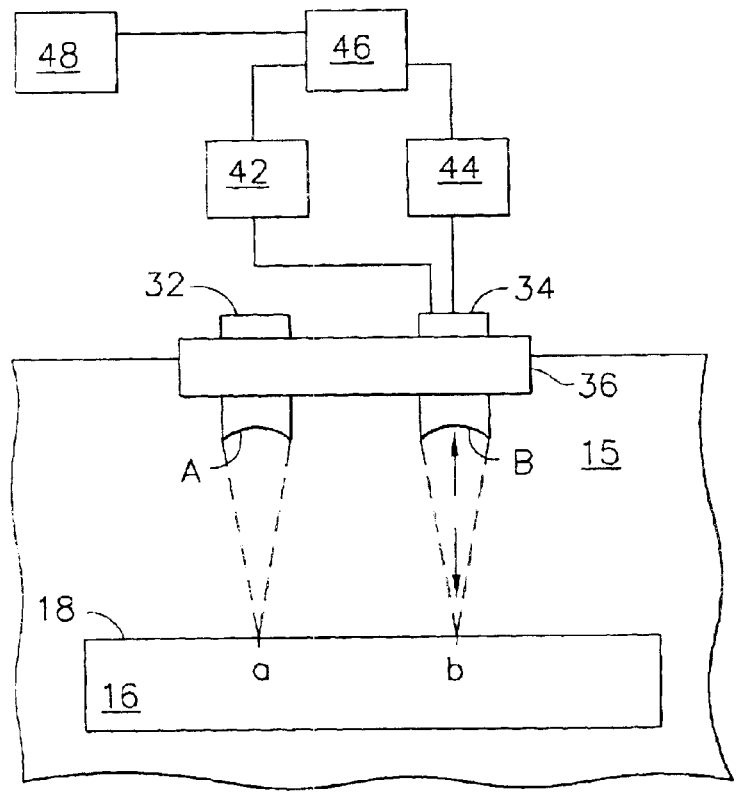
FIG. 8 is a schematic view of the ultrasonic transducer setup of the FIG. 6 illustrating a second intermediate arrangement of connections between the various components.

More than one procedure may be used to implement the subtractive measurement method of the present invention. A first exemplary procedure for performing the method of the invention, using a single pulser and receiver, is illustrated in FIGS. 6, 7, and 8. Referring to FIG. 7, the pulser 42 and the receiver 44 are first connected to one transducer, e.g., the first transducer 32. A wave (for example wave generated by a negative spike pulse of the pulser 42) is transmitted and the directly reflected wave from the point on the surface 18 of the specimen 16 that is directly under the first transducer 32 (point a) is recorded. The traveling time for this wave is twice $t_{Aa}$, where $t_{Aa}$ is the direct travel time required for the ultrasonic wave to travel from the surface of the first transducer 32, labeled A, to the surface 18 of the specimen 16.

As shown in FIG. 8, the pulser 42 and receiver 44 are then disconnected from the first transducer 32 and connected to the second transducer 34, and the steps described above are repeated for the second transducer 34. A direct reflection time is thereby obtained which is equal to twice $t_{bB}$, where $t_{bB}$ is the direct travel time required for the ultrasonic wave to travel from the surface of the second transducer 34, labeled B, to the surface 18 of the specimen 16.

After the values for $t_{Aa}$ and $t_{bB}$ are determined, the pulser is then connected to one transducer, e.g. the first transducer 32, and the receiver is connected to the other transducer, e.g., the second transducer 34, as shown in FIG. 6. By pulsing the first transducer 32, an ultrasonic wave is generated which moves toward the specimen 16. When this wave reaches the surface 18 of the specimen 16 (at the point labeled a), it creates a surface wave (schematically illustrated as item 25 in FIG. 6) with a cylindrical wave front centering at point a. This surface wave 25 continuously leaks energy back into the coupling medium 15 while moving away from point a. When part of its wave front reaches point b on the surface 18, the leakage energy at point b will travel toward the second transducer 34. Once the receiver connected to the second transducer 34 senses the arriving wave, the total travelling time $t_{AB}$ of this transmitted ultrasonic wave, from the surface A of the first transducer 32 to the surface B of the second transducer, is recorded.

Finally, the previously determined values of $t_{Aa}$ and $t_{bB}$ are subtracted from $t_{AB}$ to obtain the true surface wave traveling time $t_{ab}$ from point a to point b. The subtraction procedure is explained in more detail below.

Figure 9:
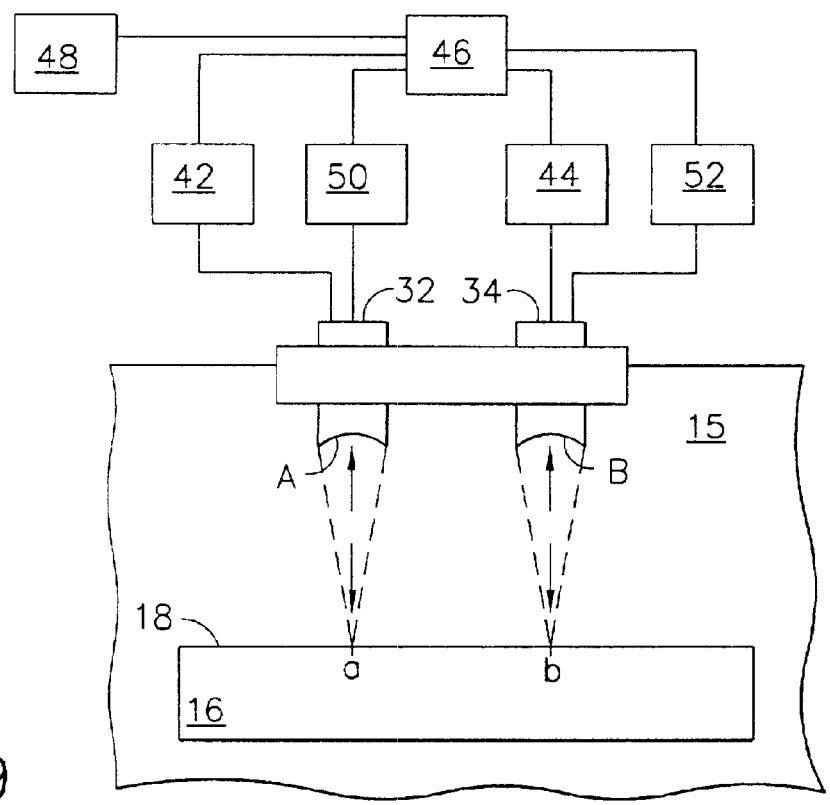
FIG. 9 is a schematic view of the ultrasonic transducer setup for practicing the method of the present invention by an alternate procedure.
Figure 10:
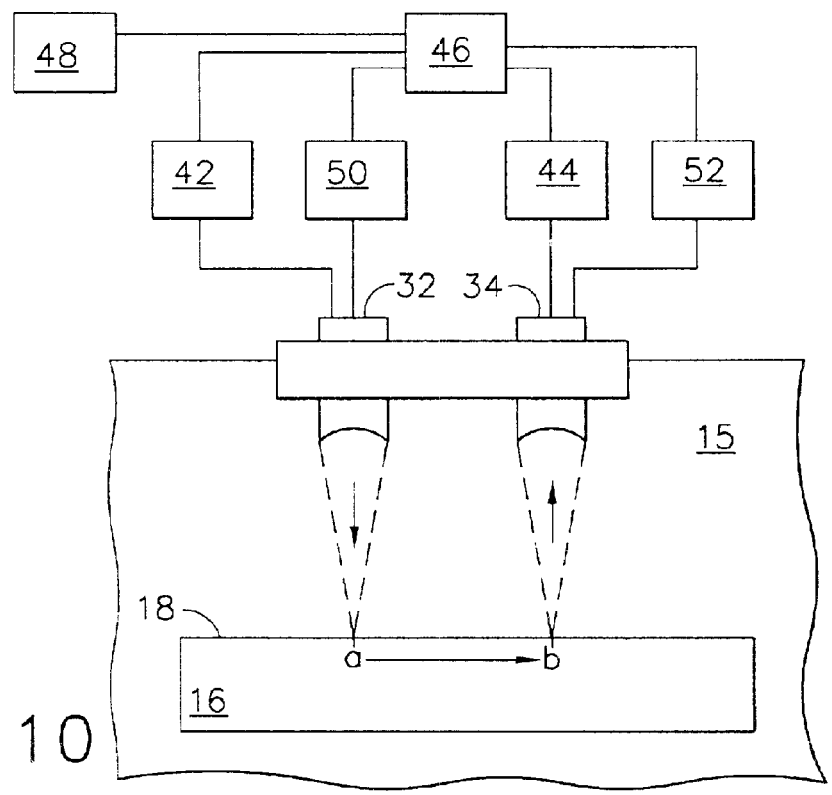
FIG. 10 is a schematic view of the ultrasonic transducer setup of FIG. 9 showing a further step in practicing the method of the present invention by an alternate procedure.

In an alternative procedure, illustrated in FIGS. 9 and 10, the method of the present invention may be practiced using two pulsers 42 and 52 and two receivers 44 and 50. A first pulser 42 and a first receiver 50 are connected the first transducer 32, while a second pulser 52 and a second receiver 44 are connected to the second transducer 34. Both transducers are pulsed and the directly reflected waves are recorded from the point on the surface 18 of the specimen 16 directly under each transducer (points a and b). This results in the direct reflection times for a wave from each of the transducers to the surface 18 and back, i.e. both twice $t_{Aa}$ and twice $t_{bB}$.

Subsequently, the receiver of one of the transducers, e.g. the receiver 50 connected to the first transducer 32, is turned off, and at the same time the pulser of the other transducer, e.g., the pulser 52 connected to the second transducer 34, is turned off. Consequently, only the first transducer 32 will transmit waves while the second transducer 34 will receive waves. The first transducer 32 is then pulsed, and the total traveling time $t_{AB}$ of an ultrasonic wave going from the surface A of the first transducer 32 and eventually arriving at the surface B of the second transducer 34 is recorded. Finally, $t_{Aa}$ and $t_{bB}$ are subtracted from $t_{AB}$ to obtain the true surface wave traveling time $t_{ab}$.

The subtraction method is now described in more detail. From FIG. 6, it can be seen that the total traveling time of an ultrasonic wave from transducer surfaces A to B is:

$$t_{AB}=t_{Aa}+t_{ab}+t_{bB} \tag{2}$$

where $t_{ab}$ is the surface traveling time of the surface wave 25 from points a to b on the specimen surface. Since both $t_{Aa}$ and $t_{bB}$ are known by measuring the direct reflected waves at both transducers 32 and 34 using the procedures described above, the surface wave traveling time $t_{ab}$ can be extracted by the following subtractive equation:

$$t_{ab}=t_{AB}-t_{Aa}-t_{bB} \tag{3}$$

This provides a simple, practical method of finding the true surface wave traveling time between two points on the surface 18 of the specimen 16. The subtraction may be performed manually, or by recording the various travel times in a known spreadsheet program and performing the subtraction procedure therein. Optionally, additional known software could be used to automate the recordation and subtraction process if desired.

The foregoing has described a method for measuring the surface travel time of a surface wave between first and second points on a surface, wherein first and second spaced apart ultrasonic transducers are disposed with their longitudinal axes substantially perpendicular to a surface. The direct travel times for each transducer are determined, then a total travel time from the first transducer to the second transducer is measured. The direct travel times are subtracted from the total travel time to produce the actual travel time between the points on the surface. While specific embodiments of the present invention have been described, it will be apparent to those skilled in the art that various modifications thereto can be made without departing from the spirit and scope of the invention as defined in the appended claims.

What is claimed is:

1. A method of measuring the surface travel time of a wave between first and second points on a surface of a specimen, comprising:

providing first and second ultrasonic transducers each having a longitudinal axis, said ultrasonic transducers being acoustically coupled to said surface and disposed in a spaced-apart relationship so that said longitudinal axes are substantially perpendicular to said surface;

transmitting a first wave from said first ultrasonic transducer and determining a first direct travel time for said first wave to travel from said first ultrasonic transducer to said first point on said surface;

transmitting a second wave from said second ultrasonic transducer and determining a second direct travel time for said second wave to travel from said second ultrasonic transducer to said second point on said surface;

transmitting a third wave and measuring a total time for said third wave to travel along a path from said first ultrasonic transducer through said first and second points to said second ultrasonic transducer; and determining said surface travel time by subtracting said first and second direct travel times from said total time.

2. The method of claim 1 wherein said ultrasonic transducers and said surface are at least partially immersed in a fluid coupling medium.

3. The method of claim 1 wherein said steps of transmitting said first wave from said first ultrasonic transducer and determining said first direct travel time, transmitting said second wave from said second ultrasonic transducer and determining said second direct travel time are performed using a single ultrasonic pulser and a single ultrasonic receiver.

4. The method of claim 1 wherein said steps of transmitting said first wave from said first ultrasonic transducer and determining said first direct travel time, transmitting said second wave from said second ultrasonic transducer and determining said second direct travel time, are performed using two ultrasonic pulsers and two ultrasonic receivers.

5. The method of claim 1 wherein the step of determining a first direct travel time comprises measuring a first direction reflection time for a directly reflected wave to travel from said first ultrasonic transducer to said first point on said surface and back to said first ultrasonic transducer and dividing said first direct reflection time by two; and the step of determining a second direct travel time comprises measuring a second direction reflection time for a directly reflected wave to travel from said second ultrasonic transducer to said second point on said surface and back to said second ultrasonic transducer and dividing said second direct reflection time by two.

6. An apparatus for measuring the surface travel time of a wave between first and second points on a surface of a specimen, comprising:

a transducer holder having first and second spaced-apart openings for receiving first and second ultrasonic transducers;

first and second ultrasonic transducers each having a longitudinal axis disposed in said openings such that said longitudinal axes are parallel to each other; and means for supporting said transducer holder such that said longitudinal axes of said first and second transducers are substantially perpendicular to said surface.

7. The apparatus of claim 6 wherein said holder comprises an acrylic resin.

8. The apparatus of claim 6 further comprising an attachment rod extending from said holder parallel to said longitudinal axes of said first and second ultrasonic transducers.

9. The apparatus of claim 8 wherein said attachment rod is mounted to an ultrasonic scanning bridge.

* * * * *